United States Patent
Morris et al.

(10) Patent No.: US 8,608,965 B2
(45) Date of Patent: Dec. 17, 2013

(54) GAS ACTUATED MIXING SYSTEM AND METHOD

(75) Inventors: Christopher Morris, Wrexham (GB); James Murcott, Bishops Castle (GB); Jonathan Tomlinson, Wrexham (GB); Richard Tomlinson, Wrexham (GB)

(73) Assignee: Farm Renewable Environmental Energy Ltd., Wrexham (GB)

( * ) Notice: Subject to any disclaimer, the term of this patent is extended or adjusted under 35 U.S.C. 154(b) by 572 days.

(21) Appl. No.: 12/918,746

(22) PCT Filed: Feb. 20, 2009

(86) PCT No.: PCT/GB2009/000499
§ 371 (c)(1),
(2), (4) Date: Nov. 10, 2010

(87) PCT Pub. No.: WO2009/104002
PCT Pub. Date: Aug. 27, 2009

(65) Prior Publication Data
US 2011/0042305 A1    Feb. 24, 2011

(30) Foreign Application Priority Data
Feb. 21, 2008    (GB) .................................. 0803111.4

(51) Int. Cl.
*C02F 3/28*    (2006.01)
*B01F 13/02*    (2006.01)

(52) U.S. Cl.
USPC ........................................ 210/603; 210/221.2

(58) Field of Classification Search
USPC ................. 210/603, 604, 220, 221.1, 221.2
See application file for complete search history.

(56) References Cited

U.S. PATENT DOCUMENTS

| | | | | |
|---|---|---|---|---|
| 1,832,469 A | * | 11/1931 | Neill et al. | 261/87 |
| 2,056,062 A | * | 9/1936 | Zack | 210/620 |
| 3,911,064 A | | 10/1975 | McWhirter et al. | |
| 4,100,610 A | * | 7/1978 | Johnston et al. | 366/102 |
| 4,179,220 A | | 12/1979 | Rippon | |
| 5,102,803 A | * | 4/1992 | Weaver | 435/290.2 |
| 6,569,332 B2 | * | 5/2003 | Ainsworth et al. | 210/603 |
| 2002/0139748 A1 | * | 10/2002 | Cote et al. | 210/636 |

FOREIGN PATENT DOCUMENTS

| | | | |
|---|---|---|---|
| DE | 1075559 B | * | 2/1960 |
| DE | 1150 028 B | | 6/1963 |
| DE | 200 10 255 U1 | | 10/2000 |
| EP | 0 338 697 A1 | | 10/1989 |

(Continued)

OTHER PUBLICATIONS

Search Report issued on May 29, 2008 in the counterpart Application No. GB0803111.4, three ( 3) pages.

*Primary Examiner* — Fred Prince
(74) *Attorney, Agent, or Firm* — Nath, Goldberg & Meyer; Jerald L. Meyer; Stanley N. Protigal

(57) ABSTRACT

A gas bubble agitated mixing system for viscous fluids comprising: a container (1) in which a viscous fluid (2) may be held; one or more gas pipes (6), each gas pipe having an outlet (8) arranged to introduce gas bubbles (9) into the base region of the container (1), said gas bubbles (9) being of a size suitable to agitate the viscous fluid (2). The system also comprises a moveable carrier arm (4) upon which said one or more gas pipe outlets (8) are mounted; and wherein the movement of the carrier arm (4) causes the position at which each outlet (8) introduces gas bubbles (9) into the container (1) to vary over time.

21 Claims, 3 Drawing Sheets

(56) References Cited

FOREIGN PATENT DOCUMENTS

| | | | |
|---|---|---|---|
| EP | 0 754 489 A1 | | 1/1997 |
| EP | 0938456 A | * | 9/1999 |
| FR | 888432 A | * | 12/1943 |
| FR | 2405090 A | | 5/1979 |
| GB | 111720 A | | 12/1917 |
| GB | 136785 A | * | 12/1919 |
| GB | 292714 A | * | 6/1928 |
| GB | 773124 A | | 4/1957 |
| JP | 8-71583 A | * | 3/1996 |
| KR | 10 2005 0029046 A | | 3/2005 |
| WO | 89/00151 A1 | | 1/1989 |

* cited by examiner

GAS ACTUATED MIXING SYSTEM AND METHOD

This is a National Phase Application filed under 35 U.S.C. 371 as a national stage of PCT/GB2009/000499, with the filing date of Feb. 20, 2009 an application claiming the benefit to the United Kingdom Application No. 0803111.4, filed on Feb. 21, 2008, the entire content of each of which is hereby incorporated by reference in its entirety.

FIELD OF THE INVENTION

The present invention relates to systems for mixing sludgy and viscous fluids. In particular the present invention relates to a gas actuated mixing system for mixing sludgy and viscous fluids, such being applicable in anaerobic digesters.

BACKGROUND OF THE INVENTION

There are numerous methods and techniques for mixing sludgy and viscous fluids, such as the sewage and organic waste that is present in anaerobic digesters. Common mixing methods utilise high speed propellers, low speed propellers or slow paddles, all of which can be placed either horizontally or vertically within the housing containing the fluid to be mixed.

Another method of mixing, known as pumped jet mixing, involves removing fluid from the container and then passing it through a pump so that it is jetted back into the container, thus causing the fluid therein to be mixed. Although the above methods can be effective at agitating the fluid within a container, such as an anaerobic digester, the energy requirements of such systems can be high. The energy requirements are further increased as the viscosity of the fluid being mixed increases.

In view of the high energy requirements when mixing more viscous fluids, a further method of mixing such fluids is sometimes used. Gas actuated mixing works by bubbling gas into the container holding the viscous fluid, usually at the base of the container. As the columns of gas bubbles rise through the fluid they agitate and mix the contents of the container. An even more efficient form of gas actuated mixing is Sequential Unconfined Gas Mixing (SUGM). This method is discussed in more detail in EP1023244.

In order to ensure that no 'dead space' is created within a container using this gas actuated mixing method there must be a suitable number of gas mixing pipes distributed within the container. By sequentially expelling gas bubbles into the container the system ensures an even flow of gas through each pipe in turn, and thus a distributed mixing effect. The pipe distribution is typically in the range of one gas mixing pipe per 5 $m^2$ of base area for low viscosity sludge, and one gas mixing pipe per 2 $m^2$ of base area for more highly viscous sludge. As a result a container with a 300 $m^2$ base plan area could require up to 150 gas mixing pipes. Increasing the number of gas mixing pipes inevitably increases the construction and maintenance costs.

As discussed above, one example of a sludgy and viscous liquid that might be suitably mixed using one of the above-mentioned mixing method is sewage sludge. In addition to the organic matter which makes up a high proportion of sewage, such waste can also comprise non-organic materials like foam, plastic and stones. These materials will either float or sink. Floating layers can be removed from the container easily using a scum trumpet. However, heavy items such as stones, grit and bits of metal will sink and build up on the base of the container. Over time the accumulated matter reduces the container volume.

In the case of anaerobic digesters, grit and deposits build up over time to such a point that the digester needs to be drained down and emptied. This will probably happen when 10 to 20% of the effective digester volume has been lost. In a 1000 $m^3$ digester, this could be 100 $m^3$ of grit, weighing about 200 tonnes. If this build-up occurs over, say, 4 years, it would represent a quantity of 140 kg of grit per day. It can take between 2 and 4 weeks to empty, de-grit, re-fill and re-start a digester. After re-starting the process it can be a further 2 to 4 weeks before stable gas production is achieved.

SUMMARY OF THE INVENTION

The present invention provides a gas bubble agitated mixing system for viscous fluids comprising: a container in which a viscous fluid may be held; one or more gas pipes, each gas pipe having an outlet arranged to introduce gas bubbles into the base region of the container, said gas bubbles being of a size suitable to agitate the viscous fluid; a moveable carrier arm upon which said one or more gas pipe outlets are mounted; and wherein the movement of the carrier arm causes the position at which each outlet introduces gas bubbles into the container to vary over time.

Preferably the system is a sequential unconfined gas mixing system. In this way the energy requirements of the system can be reduced.

In order to ensure that the gas bubbles introduced in to the mixture in the container provide agitation rather than aeration each gas pipe outlet may have a diameter of between 13-43 mm, and more preferably between 25-32 mm.

Rather than small diffuse bubbles which cling to particles causing lift, such as occur in dissolved air floatation (DAF) systems or aeration systems, the present invention provides a system where it is the mechanical force of the bubbles rising up through the fluid that physically mixes the fluid.

Preferably the carrier arm is rotatable about a fixed point. Further preferably the fixed point about which the carrier arm is rotatable is a point on the vertical central axis of the container. Alternatively the carrier arm may rotate about a fixed point located close to the wall of the container.

Preferably the carrier arm rotates at a rate of between 3 to 30 minutes for each complete rotation, and further preferably 15 minutes for each rotation. The slow rotation speed ensures that the mixing effect caused by the carrier arm as is moves through the mixture is minimised. The rotation of the carrier arm may be in one direction only. Alternatively the rotation of the carrier arm may be reciprocal in nature.

Preferably the carrier arm has an aerodynamic profile that minimises the fluid mixing effect of the carrier arm as it moves. Advantageously the orientation of at least one gas pipe outlet on the carrier arm may be oriented to direct the gas out of the leading edge of the carrier arm to reduce the amount of drag on the carrier arm.

As each gas pipe outlet moves within the container over time it defines a path of gas discharge points. This path may be linear, circular or spiral in nature dependant on the movement of the carrier arm upon which the gas pipe outlet is mounted. The gap between the discharge paths can be as high as 5 m, although a gap of 2 m is more suitable. Preferably, in mixing systems with more than one gas pipe outlet, the gap between the discharge paths of each gas pipe outlet is between 0.9 and 1.3 meters. Further preferably the gap between the paths is about 1.1 meters. This gap between the discharge paths must be balanced between minimizing the amount of pipe work within the container and maximizing the level of agitation created by gas bubbles discharged into the container.

Preferably each gas pipe only has one outlet within the container. This prevents a situation where gas escapes via the gas pipe outlet closest to the gas supply, which leads to the creation of 'dead spaces'. This enables lower power pumps to be used in the operation of the system whilst minimising the creation of 'dead spaces'.

Advantageously the carrier arm further comprises at least one scraper means, the scraper means being oriented to impart a scraping effect on at least one of the walls of the container as the carrier arm moves. The scraper means serve to move any material that have accumulated at the base of the container and prevents it settling.

Preferably the container further comprises a sump at the base thereof, the sump being positioned to receive any solid material that has accumulated at the base of the container. Further preferably the scraper means are arranged to direct the solid material towards the sump. The sump further comprises a mechanism, such as an auger, for transporting the accumulated solid material out of the container via the sump.

It is appreciated that, because the scraper and sump facilitate the removal of grit and other debris from the container, their presence enables the gap between discharge paths to be increased with impairing the performance of the system as a whole. This is possible because removal of grit means that there is less thereof to keep in suspension by agitation.

Advantageously the orientation of at least one gas pipe outlet mounted on the carrier arm may be oriented so as to direct the discharged gas towards the solid matter, thus facilitating movement of the solid matter by the scraper means.

Preferably the container in which the mixing system of the present invention is located is an anaerobic digester. Preferably in the anaerobic digester based mixing system the gas being discharged into the container is the biogas that is produced by the normal actions of the bacteria in the anaerobic digester. The biogas typically produced by anaerobic digesters comprises about 59% Methane; about 40% Carbon Dioxide and about 1% Hydrogen Sulphide, with some other minor components.

Advantageously the gas being discharged into the container may further activate any reactions taking place with the fluids in the container.

The present invention also provides a method of mixing viscous fluids within a container that has at least one gas pipe outlet on a moveable means within the base region of the container, comprising: providing a viscous, reaction mixture of organic materials and bacteria within a container; and mixing the reaction mixture by introducing gas bubbles of a size suitable to agitate the reaction mixture whilst moving the gas pipe outlets within the container, thereby varying the point at which gas bubbles are introduced into the digester over time.

Preferably the method can be carried out using the mixing system of the present invention. Preferably the container is an anaerobic digester. It is appreciated that the method can further involve the use of the products of the reactions, such as biogas, to both power the mixing system and operate the system. The mixing system of the present invention enables the user to clean out the system without having to shut it down, thus greatly reducing down-time.

BRIEF DESCRIPTION OF THE PREFERRED EMBODIMENTS

In the drawings, which illustrate exemplary embodiments of the invention:

DETAILED DESCRIPTION OF THE DRAWINGS

Figure 1:
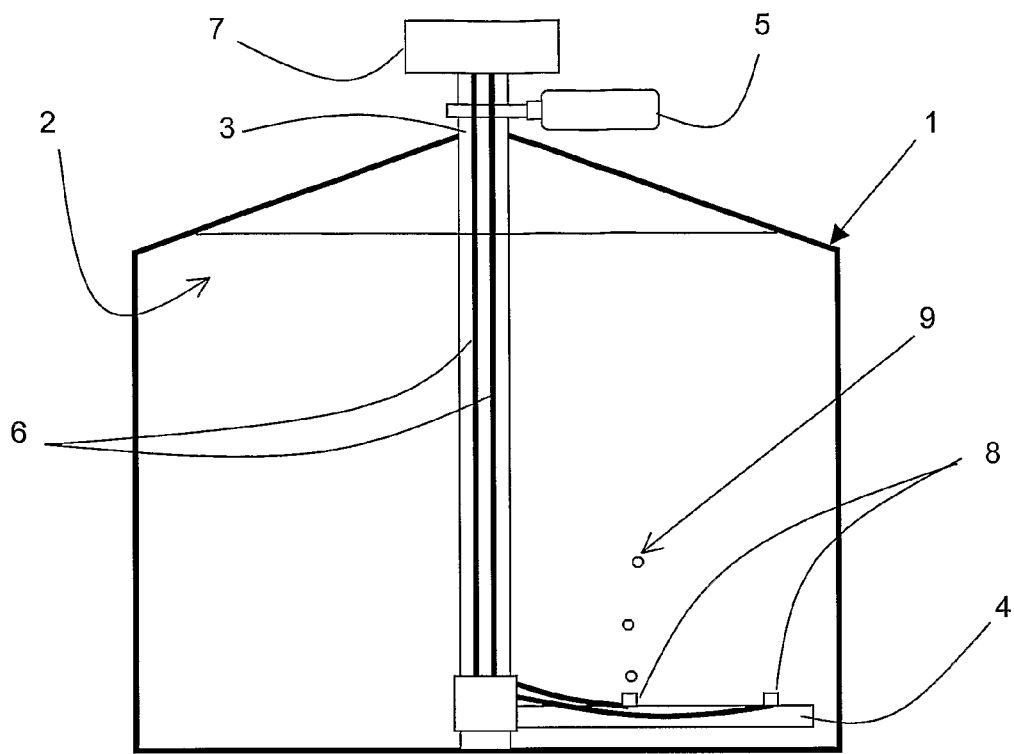
FIG. 1 shows an exposed side view of an anaerobic digester with a gas actuated mixing system.

FIG. 1 shows an embodiment of the present invention in the form of an anaerobic digester 1. Anaerobic digestion is a process in which microorganisms break down biodegradable material in the absence of oxygen. The anaerobic digester 1 holds the biodegradable material in the form of a sludgy fluid 2 in conditions suitable for the microorganisms to break down the organic matter present in the biodegradable material. The temperatures used within the anaerobic digester 1 can vary depending on the type of microbes being used.

Psychrophilic bacteria require a temperature range of between 0-20° C.; Mesophilic bacteria require a temperature range of between 20-45° C., and most commonly between 38-42° C.; and Thermophilic bacteria require a temperature range of between 45-70° C.

Thermophilic bacteria is a significantly faster process, however it has the disadvantage of being less stable making it more susceptible to kill the bacteria. The bacteria that operate in the Mesophilic band are present in most of the input materials giving a much more stable and reliable process.

Psychrophilic bacteria operate at low temperatures, however this is a slow process (as happens to manure when left to it's own devices also found on the ocean floor).

As mentioned above, it is important to constantly agitate the reaction mixture of the microorganisms and the biodegradable waste to ensure that the reaction rate is maintained at a desirable level. The present invention makes use of gas actuated mixing to agitate the reaction mixture. By bubbling gas through the reaction mixture effective agitation can be achieved with relatively low energy requirements, even with highly sludgy and viscous reaction mixtures.

It is appreciated that the wider the spread of the gas bubbles the more effective the agitation of the reaction mixture. In view of this fact, the effectiveness of a gas mixing system can be improved by increasing the number of gas bubble outlets within the anaerobic digester. Currently the number of outlets is increased by increasing the number of gas mixing pipes entering the anaerobic digester.

Figure 2:
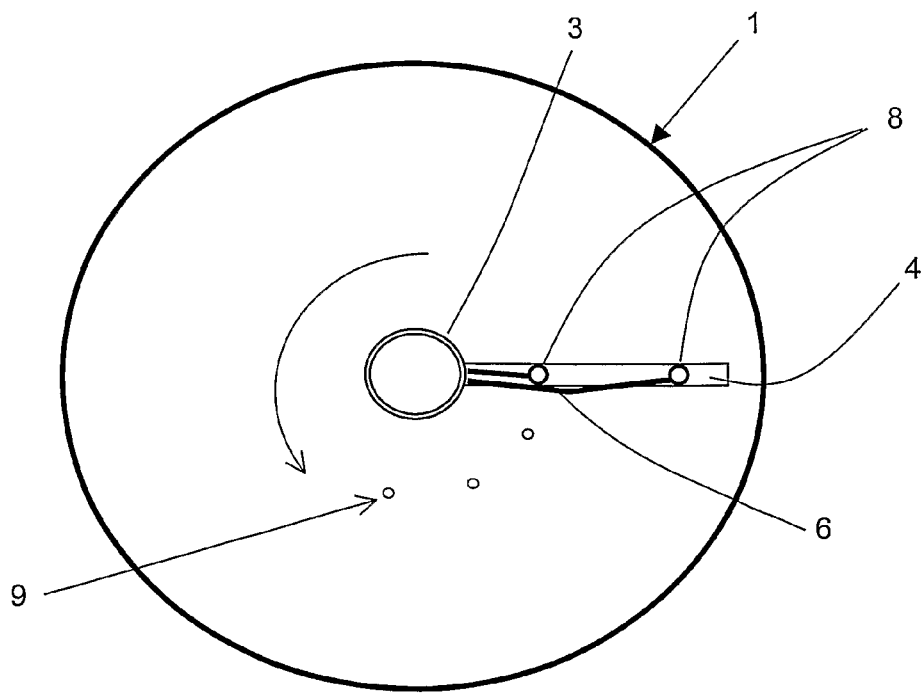
FIG. 2 show an exposed top-down view of the anaerobic digester of FIG. 1.

The anaerobic digester 1 shown in FIGS. 1 and 2, which embodies the present invention, provides an alternative approach to maximising the spread of the gas bubbles within the digester. Rather than providing a large array of gas mixing pipes within the digester, (a digester of 13.6 m in diameter can require about 72 pipes) the present invention provides a much smaller array of gas mixing pipes mounted on a moving carrier arm. In this way, as the carrier arm moves, the position of the gas pipe outlets can be varied over time, thus simulating a mixing effect similar to a larger array of gas pipe outlets.

As can be seen from FIG. 1 each gas mixing pipe 6 terminates within the base region of the digester 1 at an gas pipe outlet 8. Introducing the gas bubbles at the bottom of the digester ensures that the creation of 'dead space' is minimised. The gas pipe outlets 8 are mounted on the carrier arm 4, which is rotatably mounted within the digester 1 on a central rotating shaft 3. The central rotating shaft 3 is controlled and driven by rotation drive 5. The mechanical workings of the rotation mechanism will be appreciated by the skilled person.

The rate at which the carrier arm 4 rotates within the digester 1 can be varied depending upon the rate at which the gas is delivered into the digester 1 via the gas outlets 8. Rotations of between 1 cycle every 3 minutes and 1 cycle every 30 minutes are considered an appropriate rate. It will be appreciated that the biogas should be pumped into the system at a pressure which is at least sufficient to overcome the hydraulic head, (i.e. the height of the digester).

In order to prevent the carrier arm 4 from disrupting the reaction mixture 2 too much as it rotates, the carrier arm 4 may have a suitable aerodynamic profile. It is the intention of the inventors to minimise the displacement caused by the rotation of the carrier arm 4 within the reaction mixture 2. It is appreciated that reducing the drag on the carrier arm 4 can protect the gas pipes 6 mounted thereon from unnecessary stresses and strains as they pass through the reaction mixture 2.

The carrier arm 4 shown in the embodiment of FIGS. 1 and 2 extends in a single direction from the central rotation shaft 3. However it is appreciated that the carrier arm 4 may extend away from the central rotation shaft 3 in more than one direction; the embodiment of the present invention shown in FIGS. 3 and 4 has a carrier arm 4 which extend in two directions. It is appreciated that further carrier arms could be provided about the central rotation shaft 3 to increase the distribution of gas pipe outlets 8.

The gas pipe outlets 8 are mounted on the carrier arm 4 with a distribution of between 0.9 m and 1.3 m, and preferably the gas outlets are about 1.1 meters apart. Such a distribution of the gas outlets 4 ensures that the number of 'dead space' areas, which are not agitated by gas bubbles, is minimised. It will be appreciated by the skilled man that, when the carrier arm 4 extends in more than one direction from the central rotation shaft 3, it is the distribution of the gas bubble paths that is crucial rather than the actual distance between gas outlets 8 on any particular carrier arm 4. The path defined by the gas bubbles 9 introduced into the digester 1 as the carrier arm moves can be appreciated from FIG. 2. Although the carrier arm shown in FIGS. 1 and 2 is rotating in a single direction it is appreciated that the rotation may also be reciprocal in nature.

The delivery of the gas into the digester via the gas mixing pipes 6 and eventually through the outlets 8 is controlled by the gas control means 7. In the preferred embodiment shown each gas mixing pipe 6 supplies a single outlet 8. This ensures that gas bubbles are delivered via the outlet 8 and prevents the formation of 'dead space'. The gas control means 7 controls the pressure at which the gas is passed down the gas mixing pipes 6. The skilled person will appreciate that the control means will probably comprise a pump (or be connected thereto) to ensure that the gas is forced through the system at a suitable rate.

In order to ensure that the gas bubbles introduced into the digester via the gas pipe outlets (8) are of a suitable size to agitate the reaction mixture rather than aerate the mixture the outlets must be above a certain size. It will be appreciated by the skilled man that the outlets used to produce gas bubbles suitable for aeration are usually about 1 mm in diameter, and can sometimes be a small as 0.1 mm in diameter. It will be appreciated that the size of the outlets required to produce gas bubbles that are suitable for agitation are much bigger, and sometimes by one or more orders of magnitude.

The gas mixing pipes 6 are normally between 18-43 mm in diameter. The outlet diameter of the pipes will usually be between 32-43 mm in diameter to ensure suitable gas bubble size, although it is appreciated that outlets of 25 mm and even 18 mm could be used to provide gas bubbles that agitate rather than aerate the reaction mixture.

It is appreciated that, although the gas pipes 6 might suitably be made from ABS (Acrylonitrile butadiene styrene) or another plastic, stainless steel may also be usefully applied to make the gas pipes.

Although the delivery of gas to each of the gas pipe outlets 8 can be constant, it is appreciated that the use of Sequential Unconfined Gas Mixing (SUGM) is also suitable for the present invention. In order to provide a sequential gas supply to the gas outlets the gas control means may also comprise a valve similar to those described in EP1023244 and EP0068906. Utilising SUGM allows the system to be operated with lower energy requirements as the gas pressure only needs to be enough to supply the gas pipe outlets sequentially rather than concurrently.

It is appreciated that one of the by-products of the break down of biodegradable material by micro-organisms is Biogas. The present invention can make use of the Biogas by using it to mix the reaction mixture. It is also appreciated that alternative gases can be used, such gases could even have activating effects on the reactions taking place in the digester.

Figure 3:
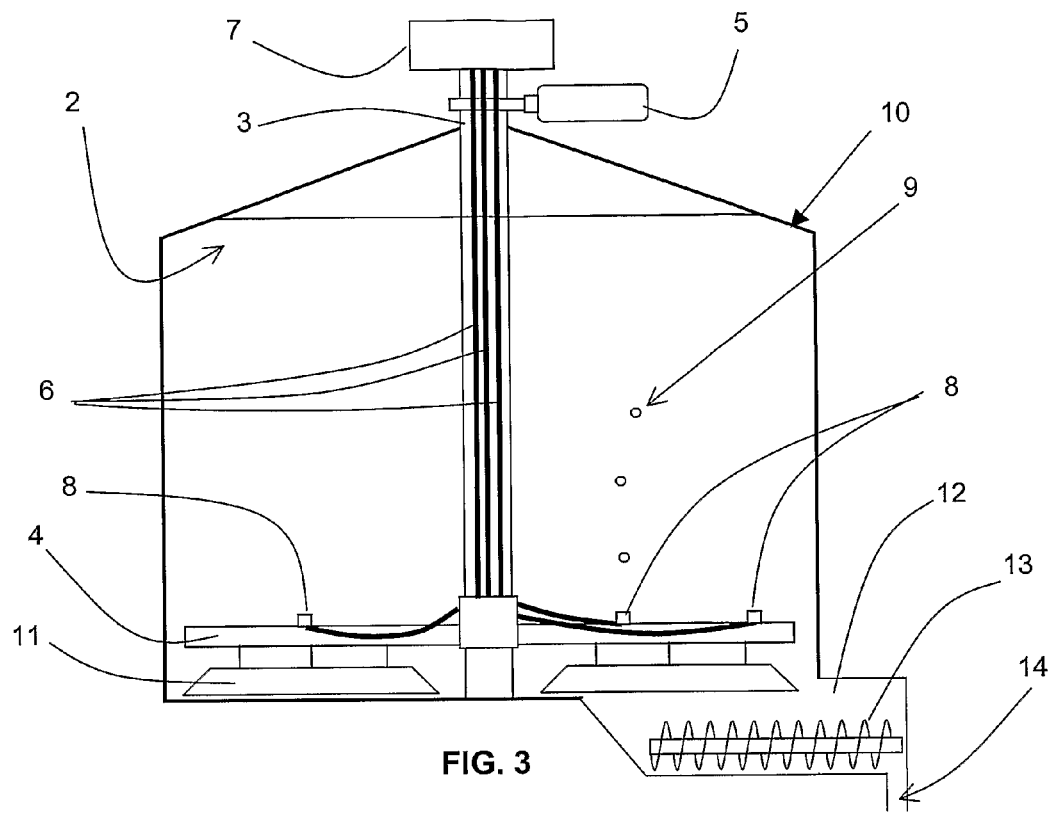
FIG. 3 shows an exposed side view of an anaerobic digester with a gas actuated mixing system and a de-gritting system.
Figure 4:
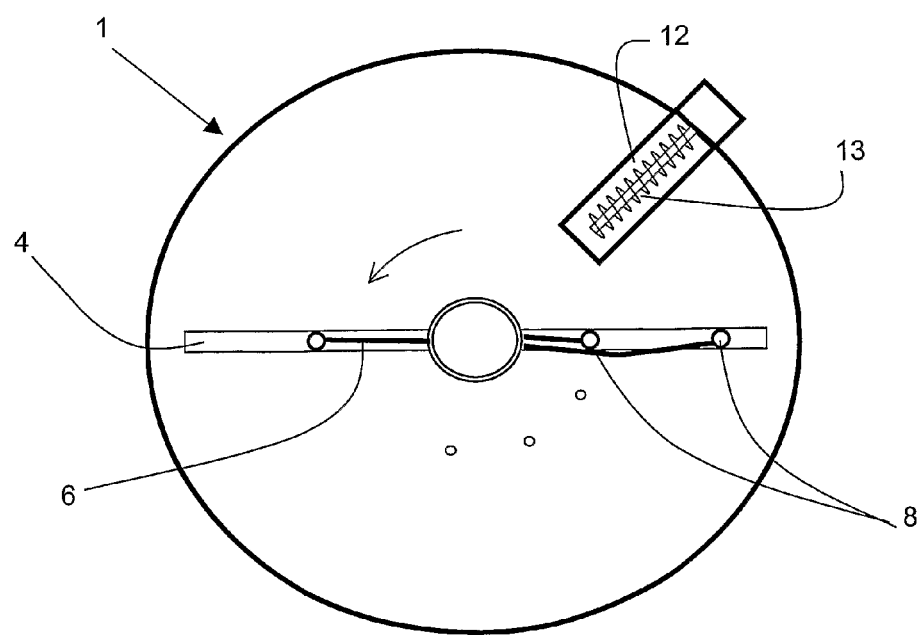
FIG. 4 shows an exposed top-down view of the anaerobic digester of FIG. 3.

FIGS. 3 and 4 show an alternative embodiment of the gas actuated mixing system of the present invention, once again in the form of an anaerobic digester 10. The anaerobic digester 10 has essentially the same gas actuated mixing system as the anaerobic digester 1 of FIGS. 1 and 2, but with the already mentioned variation in the form of the carrier arm 4. However the anaerobic digester 10 shown in FIGS. 3 and 4 further comprises a de-gritting system to help prevent the build up of solid—usually not organic—material at the base of the digester 10.

As mentioned above, over time non-organic matter such as grit and metal can accumulate at the base of an anaerobic digester. If left to build up this material can impair the performance of the digester, and eventually stop it from functioning. As a result it is necessary to periodically empty the digester and clean it thoroughly. This type of maintenance can mean that the digester is out of operation for up to 4 weeks. Due, in no small part, to the time taken to re-establish a functioning culture of micro-organisms within the digester.

The de-gritting system shown in the present embodiment works by preventing the build up of the non-organic matter or other solid materials over time. The movement of the non-organic matter is facilitated by the scraper blades 11 mounted on the underside of the carrier arm 4. As the carrier arm 4 rotates about the central rotation shaft 3 the scraper blades 11 collect the solid materials that have settled at the base of the digester 10.

The digester 10 further comprises a sump 12, which can be better appreciated from FIG. 4. The sump 12 receives the solid matter as the scraper blades 11 push it over the opening to the sump 12. The orientation of the scraper blades 11 should be maximised to direct the solid materials towards the opening of the sump 12. Located within the sump 12 is an auger 13, which gradually extracts the material from the sump 12 enabling it to exit the digester via a port 14 in the sump. It will be appreciated that alternative mechanisms might also be employed to extract the solid materials from the sump 12.

Although the gas pipe outlets 8 are pictured in FIGS. 3 and 4 are being located on the upper side of the carrier arm 4 it is appreciated that one or more gas outlets might be oriented so as to expel gas out of the leading face of the carrier arm 4. In this way the direct agitation in front of the scraper blades 11 will help to keep some of the solid materials more mobile in that area, thus increasing the amount of material pushed towards the opening of the sump 12. Such an arrangement may also improve the movement of the carrier arm 4 through the reaction mixture by producing a vacuum or suction effect in front of the leading edge of the carrier arm 4.

It is appreciated that other gas pipe outlets 8 may be oriented to help reduce the drag on the carrier arm 4 as it passes through the reaction mixture 2. By directing the flow of gas out of the leading edge it is possible to create a small 'vacuum' which sucks the carrier arm forward through the reaction mixture.

Although the embodiments described above are both containers with a flat circular base plan and a carrier arm with a circular rotational path, it is appreciated that the present invention could be equally applicable to containers of different shapes. For example, by angling the carrier arms at an angle of less that 90° to the central rotation shaft the system could be effectively used in a container with a conical base.

Figure 5:
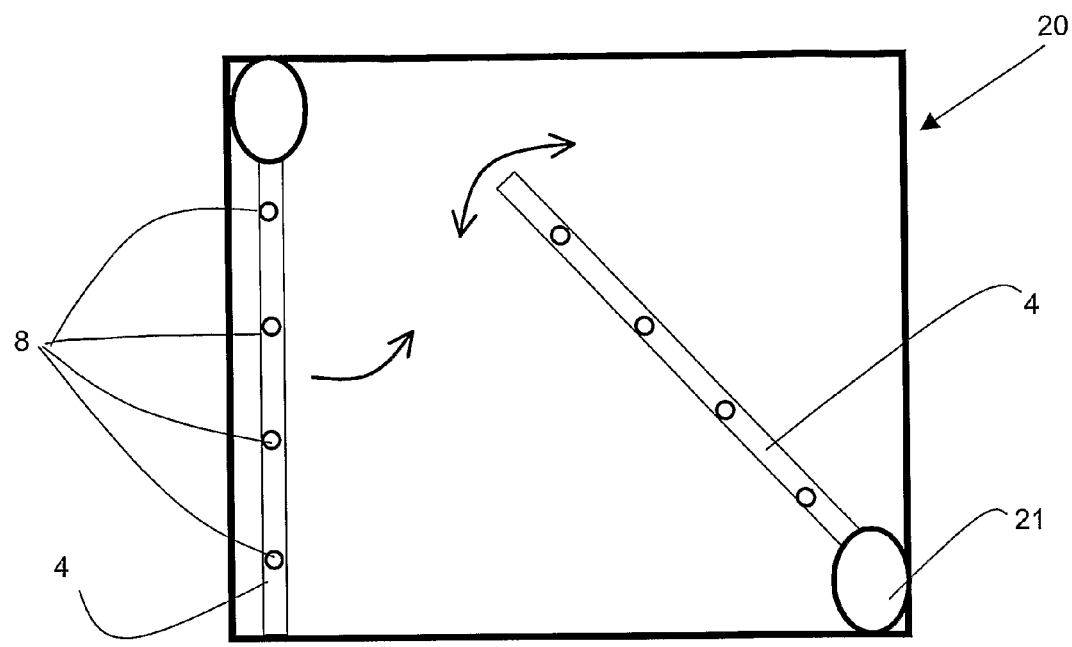
FIG. 5 shows a simplified plan view of an alternative embodiment of the present invention.
Figure 6:
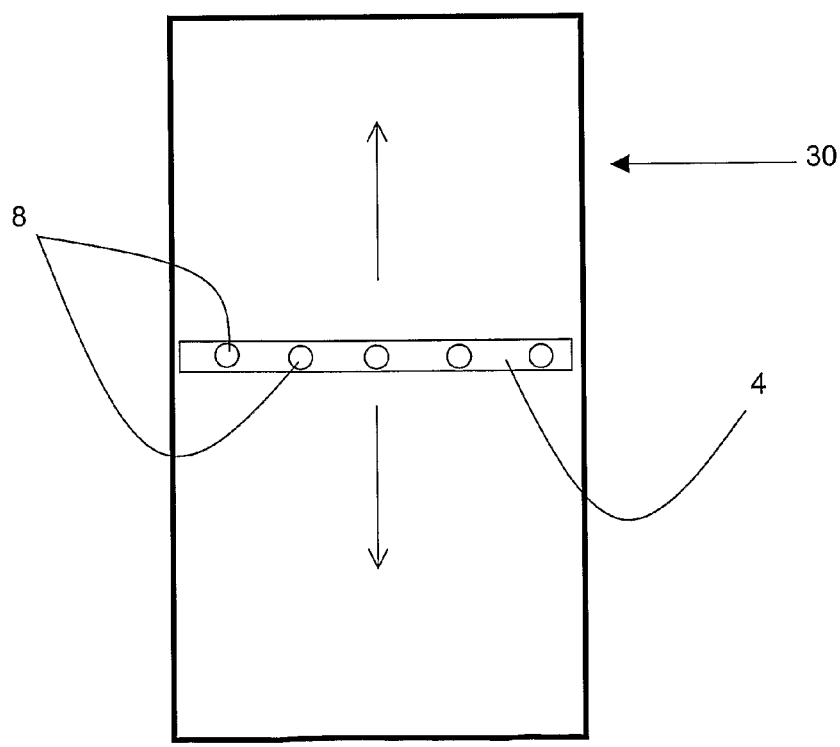
FIG. 6 shows a second simplified plan view of an alternative embodiment of the present invention

FIGS. 5 and 6 show simplified plan views of alternative arrangements of the gas actuated mixing system of the present invention. It can be appreciated from these further embodiments that movement of the carrier arm 4 within a container does not necessarily have to be about a circular path. In FIG. 5 two carrier arms 4, mounted on axes 21, sequentially move about a reciprocal arcuate path within the container 20 to ensure a maximised distribution of gas. In FIG. 6 the carrier arm 4 travels about a reciprocal linear path within the container 30.

The invention claimed is:

1. An anaerobic digester having a gas bubble agitated mixing system, said digester comprising:
   a container in which a viscous fluid that is to be digested may be held;
   a plurality of gas pipes, each gas pipe having an outlet arranged to introduce gas bubbles into the base region of the container so that as the gas bubbles rise through the fluid the gas bubbles agitate and mix the contents of the container, said gas bubbles being of a size suitable to agitate the viscous fluid;
   a moveable carrier arm having said gas pipe outlets mounted thereon, wherein the movement of the carrier arm causes the position at which each outlet introduces gas bubbles into the container to vary over time; and
   gas control means which sequentially expel gas bubbles into the container through each gas as pipe outlet in turn.

2. A mixing system according to claim 1, wherein the carrier arm is rotatable about a fixed point.

3. A mixing system according to claim 2, wherein the fixed point about which the carrier arm is rotatable is a point on the vertical central axis of the container.

4. A mixing system according to claim 2, wherein the carrier arm rotates at a rate of between 3 to 30 minutes for each complete rotation.

5. A mixing system according to claim 2, wherein the rotation of the carrier arm is in one direction only.

6. A mixing system according to claim 2, wherein the rotation of the carrier arm is reciprocal in nature.

7. A mixing system according to claim 2, wherein the carrier arm rotates at a rate of 15 minutes for each rotation.

8. A mixing system according to claim 1, wherein the carrier arm has an aerodynamic profile that minimises the fluid mixing effect of the carrier arm as it moves.

9. A mixing system according to claim 1, wherein the orientation of at least one gas pipe outlet on the carrier arm is oriented to direct the gas out of the leading edge of the carrier arm to reduce the amount of drag on the carrier arm.

10. A mixing system according to claim 1, comprising more than one gas pipe outlet, wherein each of the moving gas pipe outlets define a gas discharge path, and the gap between the adjacent discharge paths is between 0.9 and 1.3 meters.

11. A mixing system according to claim 1, wherein the container further comprises a sump at the base thereof, the sump being positioned to receive any solid material that has accumulated at the base of the container.

12. A mixing system according to claim 11, wherein the sump further comprises a mechanism, for transporting the accumulated solid material out of the container via the sump.

13. An anaerobic digester according to claim 12, wherein the mechanism for transporting the accumulated solid material out of the container via the sump is an auger.

14. A mixing system according to claim 1, wherein the carrier arm further comprises at least one scraper means, the scraper means being oriented to impart a scraping effect on at least one of the walls of the container as the carrier arm moves.

15. A mixing system according to claim 14, wherein the scraper means are arranged to direct the solid material towards the sump.

16. A mixing system according to claim 14, wherein the orientation of at least one gas pipe outlet mounted on the carrier arm may be oriented so as to direct the discharged gas bubbles towards the solid matter, thus facilitating movement of the solid matter by the scraper means.

17. A mixing system according to claim 1, comprising more than one gas pipe outlet, wherein each of the moving gas pipe outlets define a gas discharge path, and the gap between the adjacent discharge paths is about 1.1 meters.

18. A method of mixing viscous fluids within an anaerobic digester having a plurality of gas pipe outlets on a moveable carrier arm within the base region of the digester, the method comprising:
   a) providing a viscous, reaction mixture of organic materials and bacteria within the anaerobic digester; and
   b) mixing the reaction mixture by introducing gas bubbles into the base region of the digester via the gas pipe outlets so that, as the gas bubbles rise through the fluid, the gas bubbles agitate and mix the contents of the container, said gas bubbles being of a size suitable to agitate the reaction mixture, whilst moving the gas pipe outlets within the container and thereby varying the point at which gas bubbles are introduced into the container over time time,
   wherein gas bubbles are introduced via each of the gas pipe outlets in turn.

19. The method of claim 18, further comprising the step of reintroducing the gas produced by the reactions in the container to mix the viscous, reaction mixture.

20. The method of claim 18, further comprising the step of burning the methane produced by the reactions in the anaerobic digester to power the movement of the at least one gas pipe.

21. The method of claim 18, further comprising the step of extracting solid matter from the bottom of the container whilst maintaining the operation of the container.

* * * * *